US006815209B2

(12) United States Patent
Baeummer et al.

(10) Patent No.: US 6,815,209 B2
(45) Date of Patent: Nov. 9, 2004

(54) LASER-INDUCED CELL LYSIS SYSTEM

(75) Inventors: Antje J. Baeummer, Ithaca, NY (US); Mohit D. Dhawan, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 10/298,121

(22) Filed: Nov. 15, 2002

(65) Prior Publication Data

US 2003/0096429 A1 May 22, 2003

Related U.S. Application Data

(60) Provisional application No. 60/332,421, filed on Nov. 16, 2001.

(51) Int. Cl.[7] ............................ G01N 33/48; G01N 1/00
(52) U.S. Cl. ............................ 436/63; 436/174; 422/99; 435/29; 435/287.1
(58) Field of Search .......................... 436/63, 164, 174, 436/177, 180; 422/82.05, 99; 435/29, 287.1

(56) References Cited

U.S. PATENT DOCUMENTS

| | | | | |
|---|---|---|---|---|
| 4,880,512 A | * | 11/1989 | Cornelius et al. | 204/157.61 |
| 5,635,358 A | * | 6/1997 | Wilding et al. | 435/7.2 |
| 6,156,576 A | * | 12/2000 | Allbritton et al. | 436/63 |
| 6,540,895 B1 | * | 4/2003 | Spence et al. | 204/450 |
| 2002/0127604 A1 | * | 9/2002 | Allbritton et al. | 435/7.1 |
| 2003/0075446 A1 | * | 4/2003 | Culbertson et al. | 204/451 |

OTHER PUBLICATIONS

Oyog et al. Lasers in Surgery and Medicine, vol. 11 (4), 1991, pp. 372–379—see abstract.*

Liang H. Chinese Journal of Oncology, vol. 8(1), Jan. 1986, pp. 29–31—see abstract.*

Abedon, Stephen T., et al., "Lysis and the interaction between free phages and infected cells", *The Molecular Biology of Bacteriophage T4,* Washington, DC. ASM Press, Jim D. Karam, ed.,(1994), 397–405.

Baeumner, Antje J., et al., "RNA biosensor for the rapid detection of viable *Escherichia coli* in drinking water", *Biosensors & Bioelectronics, 18*(4), (Apr. 2003), 405–413.

Belgrader, P., et al., "A minisonicator to rapidly disrupt bacterial spores for DNA analysis",*Analytical Chemistry, 71* (*19*), (Oct. 1, 1999), 4232–4236.

Buer, Charles S., et al., "Insertion of microscopic objects through plant cell walls using laser microsurgery", *Biotechnology and Bioengineering, 60* (*3*), (Nov. 5, 1998), 348–355.

Clark, M., et al., "The improved lytic function and in vivo efficacy of monovalent monoclonal CD3 antibodies", *European Journal of Immunology. 19*(2), (Feb. 1989), 381–388.

De Boer, A. H., et al., "Laser microsurgery: A versatile tool in plant (electro) physiology", *Protoplasma, 178 (1–2),* (1994), 1–10.

(List continued on next page.)

*Primary Examiner*—Maureen M. Wallenhorst
(74) *Attorney, Agent, or Firm*—Nixon Peabody LLP

(57) ABSTRACT

A method of determining laser parameters for lysing cells involves exposing cells from a sub-sample of a sample to laser light. At least one parameter of the laser is varied, and damage to intracellular molecules of sub-samples of the sample at such varied parameters is measured. At least one parameter is determined based on the measured damage. In one embodiment, the laser parameters comprise power, wavelength and duration. A microchannel system provides a transport mechanism for cells to be lysed. The microchannel system is combined with a laser to lyse cells while they are being transported. The laser is disposed within a trench to expose the cells in the channels in one embodiment. In still further embodiments, the laser is integrated into a semiconductor substrate in which the channels are formed.

39 Claims, 8 Drawing Sheets

OTHER PUBLICATIONS

Dolman, D., et al., "A Kinetic Study of the Reaction of Horseradish Peroxidase with Hydrogen Peroxide", *Canadian Journal of Biochemistry, 53(5)*, (May 1975), 495–501.

Henriksen, Gordon H., et al., "Laser microsurgery of higher plant cell walls permits patch–clamp access", *Plant Physiology (Rockville), 110 (4)*, (1996), 1063–1068.

Henriksen, Gordon H., et al., "Laser–assisted patch clamping: A methodology", *European Journal of Physiology, 433 (6)*, (Apr. 1997), 832–841.

Hoffman, Franz, "Laser microbeams for the manupulation of plant cells and subcellular structures", *Plant Science, 113 (1)*, (1996), 1–11.

Kitagawa, Shinya, et al., "Manipulation of a single cell with microcapillary tubing based on its electrophoretic mobility", *Electrophoresis, 16(8)*, (1995), 1364–1368.

Kurkdjian, Armen, et al., "Non–enzymatic access to the plasma membrane of Medicago root hairs by laser microsurgery", *Journal of Cell Science, 105 (1)*, (1993), 263–268.

Lee, S. W., et al., "A Micro Cell Lysis Device", *The Eleventh Annual International Workshop on Micro Electro Mechanical Systems (MEMS)*, (Jan. 1998), 5 pages.

Miller, D. L., et al., "Photodisruptive laser nucleation of ultrasonic cavitation for biomedical applications", *Journal of Biomedical Optics, 6 (3)*, (Jul. 2001), 351–358.

Min, J. H., et al., "Highly Sensitive and Specific Detection of Viable *Escherichia coli* in drinking water", *Analytical Biochemistry. 303(2):*, (Apr. 15, 2002), 186–93.

Sims, C. E., et al., "Laser–micropipet combination for single–cell analysis", *Analyitical Chemistry, 70 (21)*, (1998), 4570–4577.

Tao, Wen, et al., "Direct gene transfer into human culutred cells facilitated by laser micropuncutre of the cell membrane", *Proceedings of the National Academy of Sciences USA, 84(12)*, (1987), 4180–4184.

Ward, M., et al., "Ultrasound–Induced Cell Lysis and Sonoporation Enhanced by Contrast Agents", *J. Acoust. Soc. Am., 105*, (1999), 2951–2957.

Wu, J., "Acoustical tweezers", *J. Acous. Soc. Am., 89*, (1991), 2140–2143.

Yeung, E. S., "Chemical Characterization of Single Cells and Single Moleculars", *J. Chin. Chem. Soc., 46*, (1999), 351–360.

* cited by examiner

LASER-INDUCED CELL LYSIS SYSTEM

This application claims the benefit of priority under 35 U.S.C. 119(e) to U.S. Provisional Patent Application Ser. No. 60/332,421, filed Nov. 16, 2001, which is incorporated herein by reference.

GOVERNMENT FUNDING

The invention described herein was made with U.S. Government support under Defense Advanced Research Projects Agency contract number MDA972-00-1-0021. The U.S. Government has certain rights in the invention.

FIELD OF THE INVENTION

The present invention relates to lysis of cells, and in particular to a system using a laser to induce cell lysis.

BACKGROUND

Bacterial pathogenesis is one of the most challenging problems worldwide, making it necessary to analyze medical, food and environmental samples for the presence of pathogenic microorganisms. Worldwide, infectious diseases account for approximately 40% of the estimated total 50 million annual deaths. A critical step in detection and identification of pathogenic organisms is very often cell lysis. In order to determine intracellular proteins such as DNA or RNA molecules to identify the organisms, a cell membrane has to be disrupted via a rapid, non-damaging and simple procedure, which ideally does not add adulterating chemicals into the cell lysate or further dilutes the sample. Each sample preparation step in a bioanalytical detection system needs to be designed carefully, especially if single cell detection is targeted. It can be expected that technology for the manipulation and analysis of single cells will play an important role in such areas as biomedical research, drug discover, diagnosis of disease and medical treatment.

Frequently used methods for cell lysis are based on mechanical, physical, chemical or biological principles. In one method, cell walls are disrupted via repeated freeze/thaw cycles, by heating of the cells to temperatures above 60° C. or by osmotic pressure. Alternatively, cells are lysed via bead milling, sonication or lyophilization. Biological lysis methods often use the enzyme lysozyme, or bacteriophages, and chemical methods utilize chaotropic agents at high concentrations. Depending on the microorganism, and on the availability of equipment, all of these procedures are currently used in research and industrial laboratories. Main disadvantages of these procedures are labor intensity, time requirement, damage to nucleic acid and proteins and also adulteration of the cell lysate with other compounds, which have to be separated from molecules of interest, such as nucleic acids and proteins.

Laser microsurgery has demonstrated that cell membranes could be destroyed locally while keeping the interior of the cell non-damaged. Wavelengths above 750 nm are typically used on a membrane of a cell that is sucked up in a patch clamp type of device. A shock wave has also been used to lyse cells by placing the cells or cellular components in a solution.

SUMMARY

A method of determining laser parameters for lysing cells involves exposing cells from a sub-sample of a sample to laser light. At least one parameter of the laser is varied, and damage to intracellular molecules of sub-samples of the sample at such varied parameters is measured. At least one parameter is determined based on the measured damage. In one embodiment, the laser parameters comprise power, wavelength and duration.

In one embodiment, the sub-sample contains between approximately 80 to 2000 cells and the intracellular molecules comprise RNA. In a further embodiment, measuring damage comprises measuring protein damage.

The wavelength parameter is varied between approximately 500 nm and 3500 nm and higher and the power parameter is varied between approximately 0.0 mW and 300 mW. The duration parameter is approximately 4 minutes but may be varied. For smaller volumes, the duration may be reduced to one second or less.

In a further embodiment, a system for laser lysing cells includes a hydrophobic surface for supporting cell samples, a laser, and a mirror and lens for directing the laser onto the cell samples. The laser has a power level variable between approximately 0.0 mW and 300 mW. The hydrophobic surface comprises an infrared card wrapped in a layer of parafilm.

In a further embodiment, a microchannel system provides a transport mechanism for cells to be lysed. Several parallel channels or a serpentine single channel are two different embodiments. The microchannel system is combined with a laser to lyse cells while they are being transported. The laser is disposed within a trench to expose the cells in the channels in one embodiment. Such a laser does not need lenses, but lenses may be used if desired. In this embodiment, exposure times of one second or less are sufficient to lyse the cells but longer exposure times may be required for different cell types. In still further embodiments, the laser is integrated into a semiconductor substrate in which the channels are formed.

DETAILED DESCRIPTION

Figure 1:
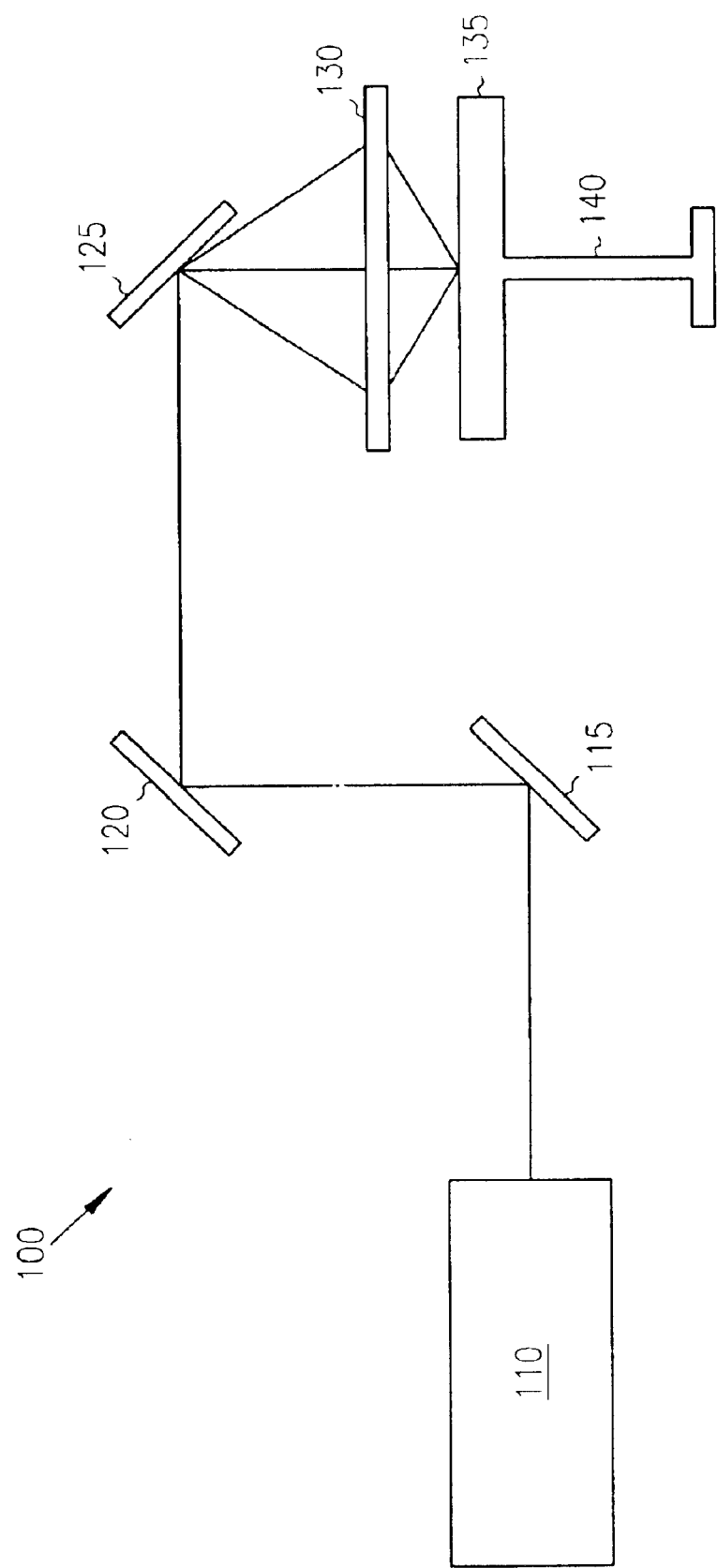
FIG. 1 is a block schematic diagram of a system for laser lysing cells.

In the following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

A method of lysing cells using a laser is described by use of several examples. Systems for transporting cells and lysing cells while being transported are then described, followed by more examples with typical results.

In one example, an experimental setup is shown in block schematic form at 100. A laser 110 is used to provide a source of laser light that is reflected by multiple mirrors 115, 120 and 125 to provide a vertical laser beam. A lens 130 is disposed in the light directly above a sample 135 supported on a stand 140. The lens focuses the laser beam onto the sample and has a focal length of approximately 75.6 mm. In one embodiment, the mirrors are flat silver mirrors, such as those available from Newport Corporation.

The sample 135 is placed on surface, which is wrapped using a single layer of parafilm in one embodiment. In one embodiment, an infrared card is used in order to visualize the laser beam. The parafilm provides a hydrophobic surface on which aqueous samples form a sphere with least contact area to the parafilm surface. This ensures consistency of sample dimensions and minimizes loss of cells due to unspecific binding to the parafilm surface.

In one embodiment, the samples 135 comprise bacteria, such as E. coli cells, with samples of low cell concentrations between 2000 to less than 200 cells per sample. Low continuous power lasers 110 were applied to minimize damaging effects of intracellular molecules due to laser treatment. Some examples of lasers include but are not limited to Argon lasers (500 nm wavelength), Titanium sapphire (800 nm), ND:YAG (1064 nm), Cr:fosterite (1250 nm), Cr:Fosterite pumped Nd:YAG Laser, and a Fiber laser (1550 nm). All lasers were continuous, except the Fiber laser, pulsed at 21 mW of power. A laser pointer (564 nm, 5 mW) may also be utilized.

The E. coli samples in one embodiment, were routinely grown on 3% Tryptic Soy broth (TSB) or agar at 37° C. as appropriate. Cells in growth phase were chosen as samples. In one embodiment, samples were diluted with TSB to obtain concentrations of 25–150 cells/$\mu$L. Experiments were carried out with 6–8 replicates. In addition, 6–8 negative controls were used for experiments to obtain an exact concentration of cells in the samples. The negative controls utilize non-treated cells. For laser treatment, 2 uL of sample were placed on the hydrophobic surface and exposed to lasers for 4 minutes. The IR card was used to position the 2 $\mu$L sample in the laser beam.

The 2 $\mu$L samples are diluted with 18 $\mu$L of 3% TSB and are plated on TSB agar plates, incubated at 37° C. (or 30° C. for S. cerevisiae) (The microorganisms are grown at their optimal temperature and growth conditions in one embodiment) overnight. Colonies formed are counted and the percent laser-induced lysis is calculated by correlating the number of colonies of laser-treated samples with those of the negative controls. In addition, 1–3 positive controls (disruption of cells via sonication, i.e. 200 $\mu$L of sample are sonicated for 45 seconds at 20 W), which results in all cases in complete lysis of the E. coli cells.

A horseradish peroxidase activity assay protocol is used to determine enzyme activity. This provides an indication of whether proteins are denatured during the lysis. A 0.25 U/ml of horseradish peroxidase in water solution is added to a mixture of 1.5 mL 1.7 mM $H_2O_2$ in 0.2 M phosphate buffer, pH 7.0, and 1.4 mL 2.5 mM 4-aminoantipyrine with 0.17 M phenol. The reaction was monitored at $\lambda$=510 nm for approximately 4 minutes. As a negative control (i.e. denatured protein), the enzyme solution is incubated at 90° C. for 10 minutes prior to determining the catalytic activity.

RNA release from laser treated E. coli cell samples is determined by the detection of one specific mRNA sequence. Protocols for the detection of an mRNA sequence of heat shock protein hsp70 involve first inducing the cells to produce the mRNA. Subsequently, the cells are lysed using sonication or laser treatment. RNA is extracted and purified from the lysate mixture. The amplified RNA is detected using agarose gel electrophoresis and an E. coli specific biosensor. The biosensor assay is based on the hybridization of amplified RNA molecules with two sets of DNA probes. One set of probes (capture probes) is immobilized on a polyethersulfone membrane in the capture zone. The other set of probes is coupled to the outside of dye-encapsulating liposomes. Thus, the concentration of RNA correlates directly to the number of liposome molecules bound in the capture zone. The signals are quantified using a portable reflectometer in one embodiment, or any other suitable device in order to get a digital number for the intensity of the signal that can also be observed visually.

Figure 2:
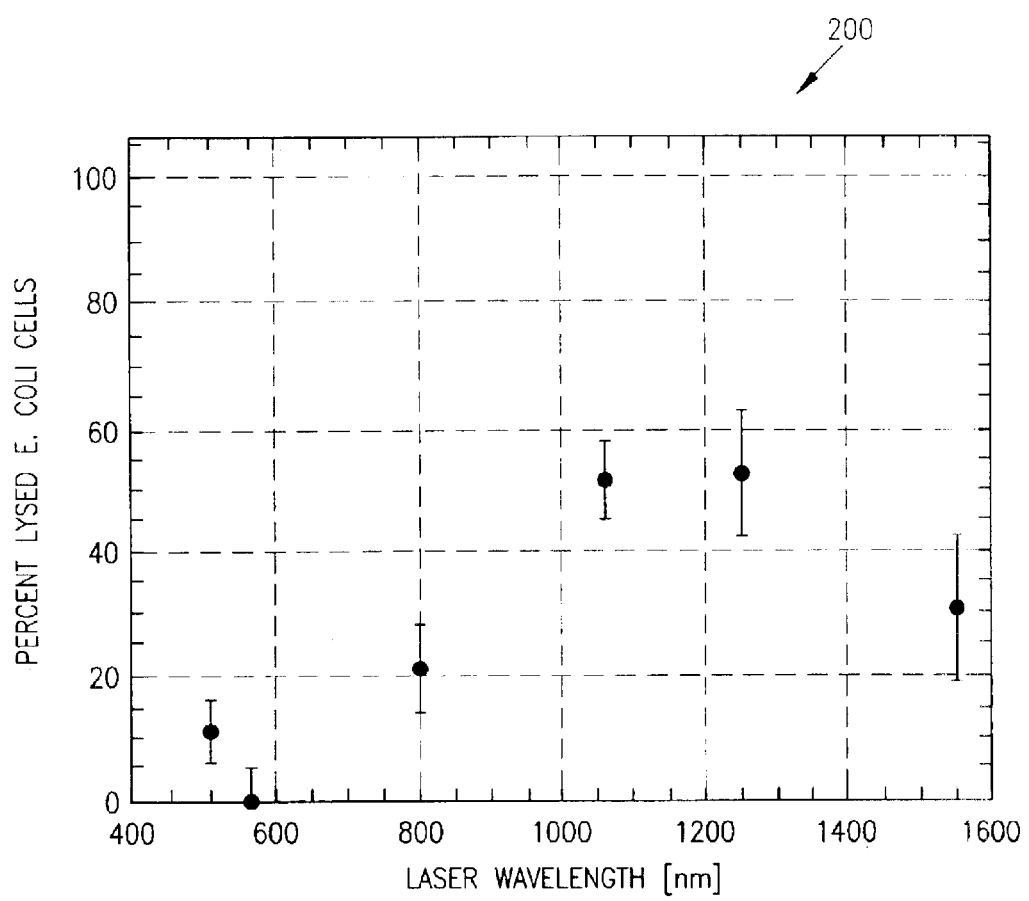
FIG. 2 is a graph of cell lysing versus laser wavelength for a given average laser power.

In a first set of experiments, E. coli cells were exposed to lasers of different wavelengths for 4 minutes. Results are shown at 200 in FIG. 2. The laser pointer resulted in no measurable cell lysis; however, all other lasers investigated had an apparent effect on the survival of E. coli cells after the exposure. The treatment appeared most effective at 1250 nm (100 mW), however, at 1550 nm 30% of the cells were lysed with only 21 mW of power. Thus, a wavelength of between 1064 and 1550 nm is effective in lysing E. coli cells. Higher wavelengths may also be effective, since water absorbs in the near infrared. In one embodiment, wavelengths up to 3050 nm to 3500 nm, are believed effective. In still further embodiments, wavelengths of 5000 nm or more may demonstrate effects.

Figure 3:
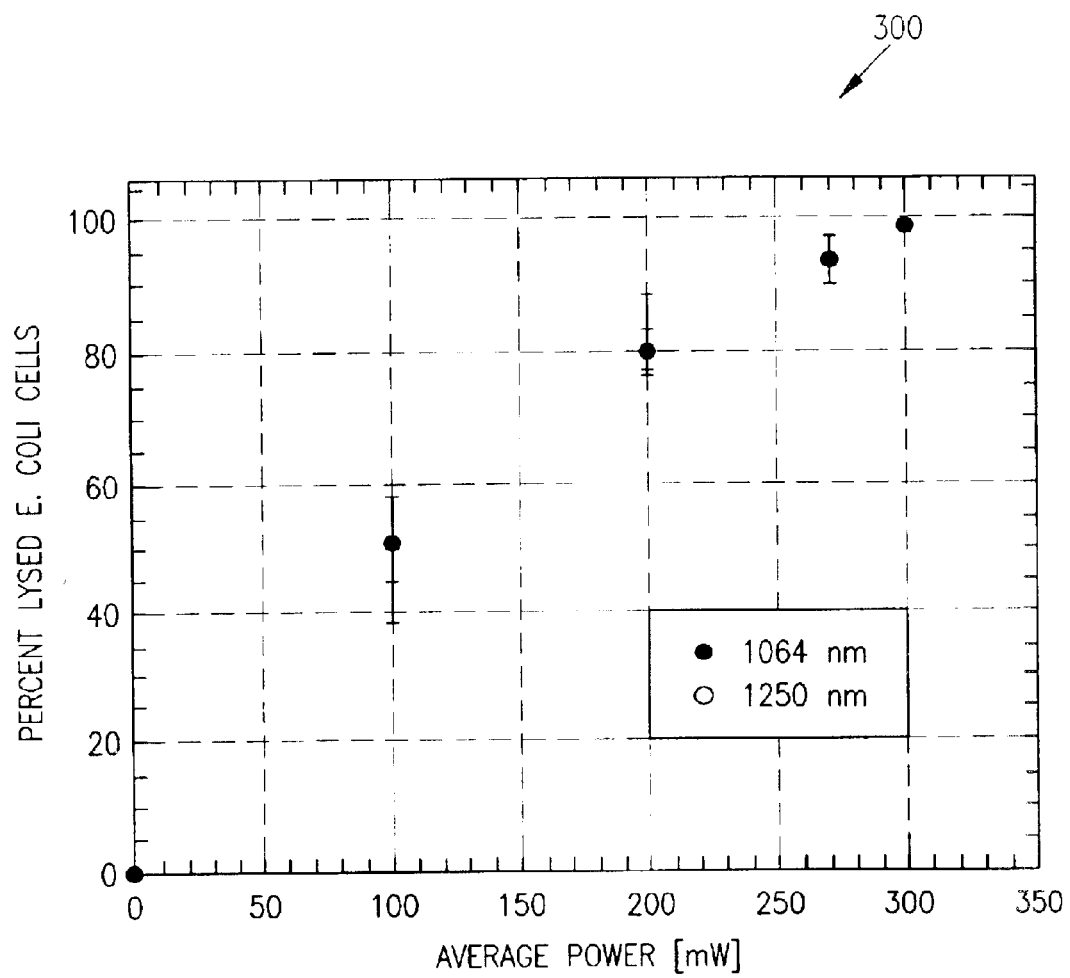
FIG. 3 is a graph of cell lysing versus average power for given laser wavelengths.

In a second set of experiments, the influence of laser energy input was investigated. As shown at 300 in FIG. 3, increasing energy input between 0 and 300 mW resulted in increased lysed cells at 1064 nm and 1250 nm. About 80% of cells were dead or effectively lysed, after exposure to 200 mW lasers, and 99.8% cells after exposure to 300 mW for 4 minutes. Since the laser-lysis system will be utilized in miniaturized sample preparation systems, low power lasers will be used.

In a third set of experiments, the denaturing effect of laser-induced cell lysis was investigated using a pure protein solution. Since intracellular proteins are located proximate a cell's membrane, the use of pure protein solutions means to have proteins without a protective shell surrounding them, and is in fact a worst-case scenario. Horseradish peroxidase was chosen as a model protein since its denaturation can be monitored by determination of its catalytic activity. 4-aminoantipyrine was used as hydrogen donor in the peroxidase reaction. The product formed is monitored in a spectrophotometer at $\lambda$=510 nm. Non-denatured protein is assumed to have 100% catalytic activity, while increasing protein denaturation results in decreasing catalytic activity.

Figure 4:
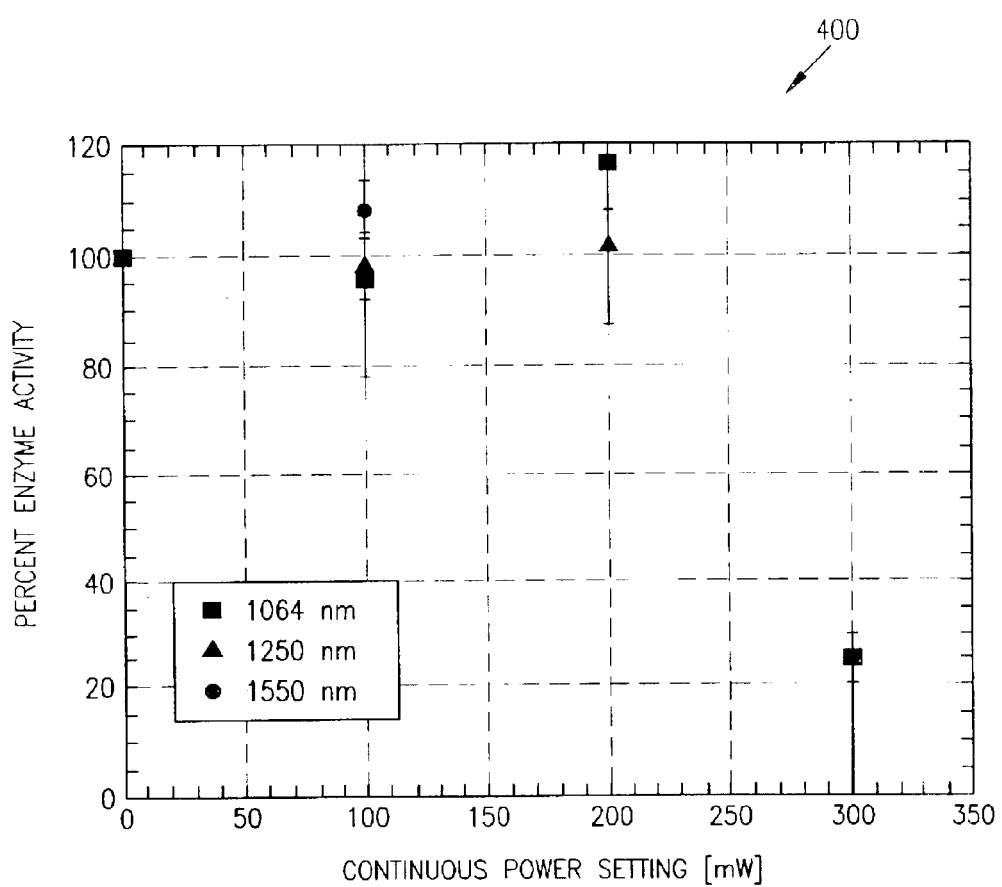
FIG. 4 is a graph of measured enzyme activity versus average power for given laser wavelengths.

In FIG. 4 at 400, the remaining catalytic activity of horseradish peroxidase exposed to lasers of different wavelength and energy input is plotted versus energy input. No loss in catalytic enzyme activity was detected at laser-induced lysis conditions for lasers between 1064 nm and 1550 nm wavelength and energy input of 100 mW and 200 mW. However, a dramatic loss in activity is found at 300 mW. It appears that conditions resulting in a significant percentage of lysed cells do not denature proteins as long as an energy input below or at approximately 200 mW is used.

In a fourth set of experiments, the release of nucleic acid molecules from laser-induced lysed E. coli cells was investigated. In previous experiments, survival of E. coli cells was used to determine damage/lysis of the cells after laser treatment. To determine that cells were actually opened and intracellular molecules released, an E. coli specific biosensor based on mRNA detection was employed to investigate mRNA release. E. coli cells were lysed using wavelengths of 1064 nm (100 mW), 1250 nm (100 mW) and 1550 nm (21 mW). A negative control consisted of the same concentration of E. coli cells, which were not treated with any laser. A positive control was made of the same E. coli solution, which was sonicated to result in lysed cells. All samples were prepared for and detected with the E. coli specific biosensor and via agarose gel electrophoresis. Table 1 summarizes the data. All laser treatments resulted in expected signals, the positive control was positive and the negative control was negative, showing that mRNA is actually released from laser-induced lysed E. coli cells.

TABLE 1

| Sample Identification | Biosensor signal (arbitrary units) |
| --- | --- |
| E. coli exposed to 1064 nm laser | 3 positive out of 3 samples |
| E. coli exposed to 1250 nm laser | 2 positive out of 3 samples |
| E. coli exposed to 1550 nm laser | 2 positive out of 3 samples |
| Positive control (sonication) | Positive |
| Negative control (no treatment) | Negative |

Finally, laser-induced lysis was investigated using four additional microorganisms, B. cereus, B. subtilis, M. luteus and S. cerevisiae. These organisms were treated as described previously for E. coli with laser wavelengths above 1000 nm, and their survival was determined subsequently using nutrient agar plates. The results are summarized in Table 2. All microorganisms showed laser-induced lysis, as effectively as demonstrated with E. coli. B. subtilis may have been an outlier in the data or may just behave differently.

TABLE 2

| Bacteria | 1064 nm laser (100 mW) | 1250 nm laser (100 mW) | 1550 nm laser (21 mW) |
| --- | --- | --- | --- |
| Bacillus cereus | 45.4% | 53.35% | 19.2% |
| Bacillus subtilis | 11.8% | 16.5% | 7% |
| Saccharomyces cerevisiae | 44.7% | 54.2% | 14.9% |
| Micrococcus luteus | 48.8% | 56.2% | 28.1% |

A mammalian cell line, J774, was also investigated using the Yag laser (i.e. 1064 nm) at three power settings: The percent lysis was:

22% (100 mW)
31% (200 mW)
56% (300 mW).

Figure 5:
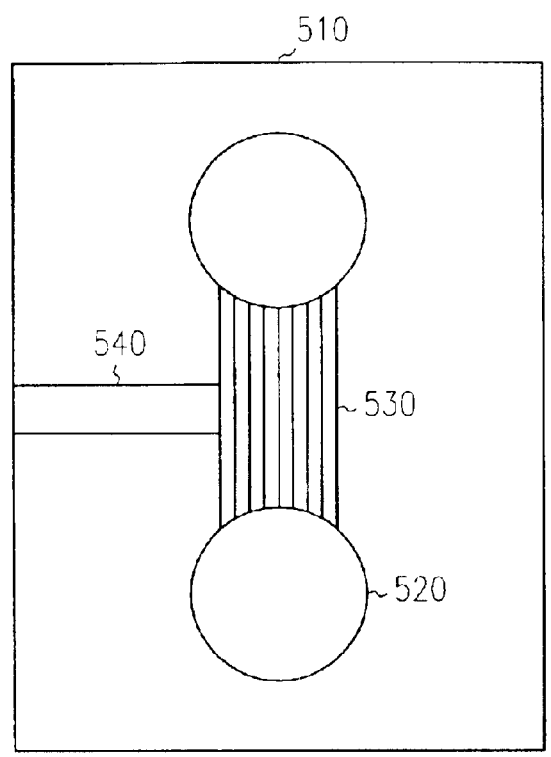
FIG. 5 is a top view of a representation of a microchannel system for transporting cells to be lysed between an input and an output well.
Figure 6:
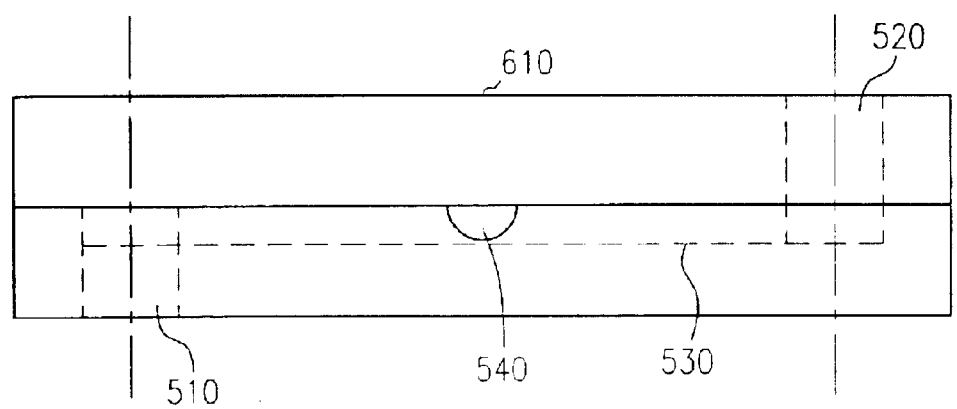
FIG. 6 is a side view of the microchannel system of FIG. 5.

One embodiment of a microchannel system is shown at 500 in FIG. 5, a top view, and FIG. 6 a side view. System 500 is fabricated in silicon, PDMS (polydimethylsiloxane) or PMMA (polymethylmethacrylate). Silicon is hydophobic, resulting in low cell loss, and has a low absorption of infrared light. PDMS is transparent to infrared light, and is easy to fabricate. An input well 510 is coupled to an output well 520 via microchannels 530. In one embodiment, microchannels 530 comprise 25 approximately parallel channels that are approximately 2 cm long, 50 $\mu$m wide, and 100 $\mu$m deep. Substantially perpendicular to the channels is a trench designed to house an optical fiber. The trench is approximately 3 cm long, 125 $\mu$m wide and 100 $\mu$m deep. A slab of PDMS 610 is placed on top of the microchannels 530.

In one embodiment, system 500 is initially made as a negative in silicon on a 4" wafer using standard photolithography and silicon etching techniques. Subsequently, the elastomer polydimethylsiloxane (PDMS) is used to transfer the negative image into a positive structure. Thus, PDMS blocks bearing the device structure with the above-mentioned dimensions are prepared. A thin layer of PDMS is used to seal the channels by treating them with a 2-minute oxygen plasma to oxidize the surface of the PDMS. Six mm holes are punched into the covering PDMS piece as inlet and outlet holes or wells 510 and 520. Outlet holes are punched in the PDMS piece carrying channels.

A second microchannel device 700 consists of one serpentine channel 730 between an input 710 and an output 720. A laser trench 740 is positioned so that each channel will be exposed by it. The channels are approximately 50 $\mu$m wide, 100 $\mu$m deep. In one embodiment, the laser trench is positioned near an end of a first column of the serpentine channel 730. In further embodiments, it is positioned at any point along an outside column, or end of a column, such as parallel with the column or otherwise positioned to sufficiently illuminate the entire sample flowing through the serpentine pattern. In yet a further embodiment, straight channels are formed, and the laser beam goes along the channel instead of perpendicular to it, so that the solution is exposed to the laser beam throughout its traveling time in the channel. Many other designs may also be utilized.

The channels may be formed in many different manners. In one embodiment, a PDMS channel is formed in the following manner. Resist is spun on a silicon wafer in three stages. The wafer is spun at 500 rpm for 3 seconds and in a second stage the resist is spun on the wafer at 3800 rpm for 45 seconds and in the third stage, at 500 rpm for 3 seconds to obtain a 2.7 microns think uniform layer of resist.

Primer spin: Before spinning the resist the primer P-20 is spun in the same three stages.

Prebake: The resist is prebaked at 115° C. for 90 seconds.

Lithography: Contact aligner is used to expose the resist for 8 seconds.

Postbake: The wafer is postbaked at 115° C. for 90 seconds.

Resist development: The resist is developed using AZ-MIF300 for 60 seconds and then the wafer is washed in water and dried using a $N_2$ gun.

Silicon etching: Once the pattern is developed and observed under the microscope the wafer is etched for silicon for 60 minutes to obtain 100 micron deep trenches in Silicon in Unaxis 770.

Descum: After the silicon etch the wafer is descummed to take off residual resist and residue from silicon etch.

Resist strip: After desumming the wafer the wafer is stripped off of the resist at 65° C. for 20 minutes because PDMS binds with the resist if not stripped properly.

PDMS channels are formed by pouring a mixture of the elastomer and the curing agent on the Si wafer and curing for an hour at 60° C. Channels are then peeled off from the Si surface. This layer peeled off from the wafers can be cut to obtain individual devices. A tray with a flat base is used to form a stand for the channels.

Polydimethylsiloxane is a transparent polymer. The transparency of PDMS to infrared light allows laser light to pass through the PDMS before it comes into contact with cell carrying solution. Using a clear field mask and various microfabrication techniques like photo-lithography, and silicon etching the complement of the channels 530 is formed on the silicon wafer. The first device is shown in FIGS. 5 and 6 with 25 channels running in parallel. In one embodiment, the channels are 2 cm long, 50 $\mu$m wide, and 100 $\mu$m deep. The trench 540 in one embodiment is 3 cm long, 125 $\mu$m wide and 100 $\mu$m deep trench running perpendicular to which serves as a coupling holder for the optical fiber from the laser.

For individual devices, a flat slab of PDMS is placed on top of the channels. These two layers are bound together by oxidation of the surfaces of the two PDMS layers using for example a TESLA coil. The surface of PDMS is oxidized for about 2 minutes each to obtain an irreversible bonding. The input wells are 6 mm diameter holes drilled in the cover layer of PDMS in one embodiment. An output orifice, which is 6 mm hole drilled at the other side in the channel carrying layer of PDMS. The output well is bonded using oxidation to a polyacrylamide device connected to a suction mechanism.

The cell solution is introduced in the input well using a pipette and the suction mechanism pulls the solution through the channels where the cells would be lysed using the laser light. Approximately 25% of the input power is absorbed in the channels as well as the cell solution out of which the power absorbed by the PDMS channels is miniscule. Since about 75% of the power is not absorbed, the number of channels may be increased.

Figure 7:
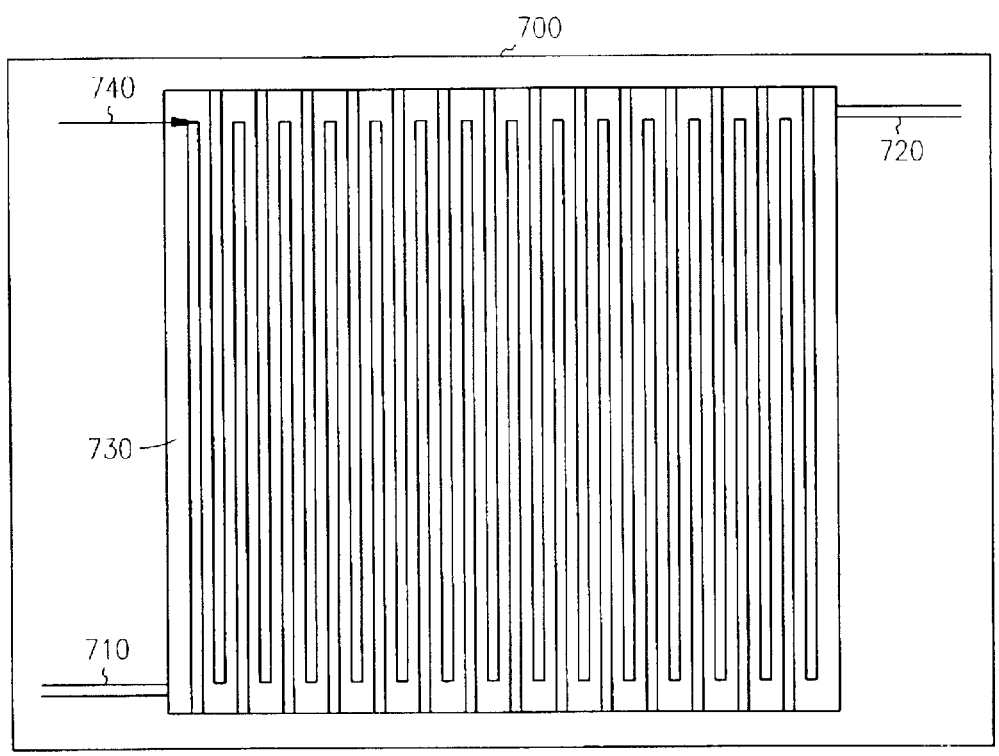
FIG. 7 is a top view of an alternative representation of a microchannel system for transporting cells to be lysed between an input and an output well.

Cells are lost in both design one corresponding to FIGS. 5 and 6, and design two corresponding to FIG. 7. With a flow rate=2 $\mu$l/minute and an outer diameter, O.D.=0.35, and a number of dilutions of the initial cell solution=1:10$^3$, the following results were obtained:

| | Positive control | cell count | After flowing | cell count |
|---|---|---|---|---|
| | a1 | 510 | A1 | 479 |
| | a2 | 517 | A2 | 498 |
| | a3 | 515 | A3 | 484 |
| | a4 | 491 | A4 | 454 |
| | a5 | 479 | A5 | 476 |
| | a6 | 520 | A6 | 457 |
| | | | A7 | 489 |
| Mean | | 505.33 | | 476.71 |
| Std dev | | 16.52 | | 16.16 |

Approximately 6% of cells are lost in channels, which is likely caused by adhesion to channel walls and losses in the device and the suction assembly. These losses have been considerably reduced by flushing with 3% TSB.

In design two, with a flow rate=1 $\mu$l/minute, O.D.=0.37, and number of dilutions of the initial cell solution=1:10$^3$, the following results were obtained:

| | Positive control | cell count | After flowing | cell count |
|---|---|---|---|---|
| | a1 | 551 | a1 | 498 |
| | a2 | 527 | a2 | 491 |
| | a3 | 510 | a3 | 483 |
| | a4 | 542 | a4 | 527 |
| | a5 | 533 | a5 | 511 |
| | a6 | 546 | a6 | 417 |
| | a7 | 328 | a7 | 494 |
| | a8 | 572 | a8 | 118 |
| Mean | | 513.62 | | 488.71 |
| Std dev | | 19.32 | | 34.77 |

Approximately 5% of the cells are lost due to similar effects as in design one.

When the devices are formed in silicon, the transparency of silicon to infrared light is an important criterion because the laser light needs to pass through the silicon before it comes into contact with cell carrying solution. Using a dark field mask and various microfabrication techniques like photo-lithography, and silicon etching channels are formed on the silicon wafer. As can be seen from FIGS. 5 and 6, 25 channels are running in parallel in design one. The channels are 2 cm long, 50 $\mu$m wide, and 100 $\mu$m deep. Also a 3 cm long, 125 $\mu$m wide and 100 $\mu$m deep trench runs substantially perpendicular to the channels and serves as a coupling holder for the optical fiber from the laser. A silicon wafer is also used as a ceiling for the microchannels.

For individual devices a flat slab of silicon is placed on top of the channels. These two layers are bound together by a poly acrylic material that works as a binder.

For the input and output wells, a layer of PDMS is poured on top of these two layers of silicon and the wells are simply 6 mm diameter holes drilled in this cover layer of PDMS. The output orifice is a 6 mm hole drilled at the other side in the channel in the covering layer of PDMS. The output well is bonded using oxidation to a polyacrylamide device connected to a suction mechanism.

Figure 10:
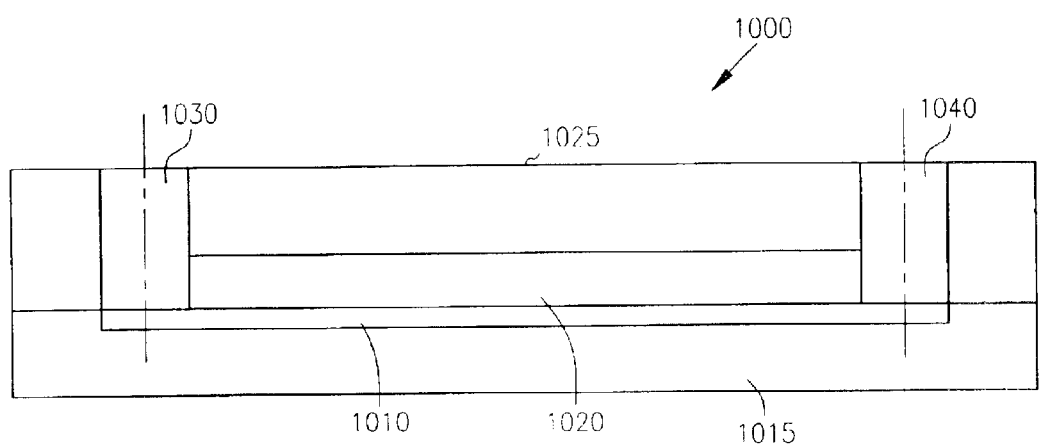
FIG. 10 is a side view of an alternative microchannel system.

FIG. 10 is a side view of an alternative microchannel system 1000. Microchannels 1010 are formed in a silicon substrate 1015 as previously described. A top piece of silicon 1020 is placed over the silicon channels, and a layer of PDMS 1025 is formed over the top piece of silicon 1020 and the substrate 1015. An input well 1030 is formed through the PDMS and top piece of silicon to contact one end of channels 1010. An output well 1040 is formed at the other end of the channels. The input and output wells provide access to the channels for introduction and extraction of samples. In one embodiment, microchannels 1010 comprise 25 approximately parallel channels that are approximately 2 cm long, 50 $\mu$m wide, and 100 $\mu$m deep. A trench may also be incorporated as shown in FIG. 5.

In one embodiment, the PDMS layer 1025 is formed by pouring it on top of the silicon layers, top piece 1020 and substrate 1015. The wells are simply 6 mm diamter holes drilled in the cover layer of PDMS 1025. In a further embodiment, an output orifice is a drilled on the other side of the channels in the covering layer of PDMS. The output well is bonded using oxidation to a polyacrylamide device connected to a suction mechanism.

The cell solution is introduced in the input well using a pipette and the suction mechanism pulls the solution through the channels where the cells would be lysed using the laser light.

In design one, with a flow rate=2 $\mu$l/minute, O.D. of 0.4, and number of dilutions of the initial cell solution=1:10$^3$, the following results were obtained:

|        | Positive control | cell count | After flowing | cell count |
|--------|------------------|------------|---------------|------------|
|        | a1               | 550        | a1            | 507        |
|        | a2               | 500        | a2            | 491        |
|        | a3               | 498        | a3            | 417        |
|        | a4               | 516        | a4            | 517        |
|        | a5               | 571        | a5            | 216        |
|        | a6               | 529        | a6            | 596        |
|        | a7               | 518        | a7            | 500        |
|        |                  |            |               | 511        |
| Mean   |                  | 526        |               | 469.37     |
| Std dev|                  | 26.56      |               | 52.37      |

Approximately 11% of cells are lost.

In design two, with a flow rate=1 µl/minute, O.D.=0.32, and number of dilutions of the initial cell solution=1:10³, the following results were obtained:

|        | Positive control | cell count | After flowing | cell count |
|--------|------------------|------------|---------------|------------|
|        | A1               | 499        | a1            | 457        |
|        | A2               | 478        | a2            | 486        |
|        | A3               | 484        | a3            | 473        |
|        | A4               | 452        | a4            | 207        |
|        | A5               | 489        | a5            | 316        |
|        | A6               | 403        | a6            | 488        |
|        | A7               | 521        | a7            | 438        |
|        |                  |            |               | 471        |
| Mean   |                  | 475.14     |               | 447        |
| Std dev|                  | 38.05      |               | 60.27      |

Approximately 6% of cells are lost in the channels.

Devices made in PMMA are made practically the same way as the devices in PDMS except instead of pouring PDMS, the surface of the silicon wafer is embossed using an embosser at an elevated temperature. Also since dry etch is performed to etch silicon, ridges are produced on the sidewalls of the channels. To smooth the ridges, the channels are coated with a thin layer of Teflon.

In some devices made in PMMA, the silicon wafer may break after embossing. Even after coating with Teflon some small pieces of broken silicon are found in the channels. The above method works in the fabrication of design one, but design two is more difficult to produce. Nonetheless, PMMA is a possible substrate as are other materials, such as glass, transparencies, other polymers etc.

In design one, with a flow rate=2 µl/minute, O.D.=0.40, and number of dilutions of the initial cell solution=1:10³, the following results were obtained:

|        | Positive control | cell count | After flowing | cell count |
|--------|------------------|------------|---------------|------------|
|        | a1               | 551        | a1            | 487        |
|        | a2               | 541        | a2            | 498        |
|        | a3               | 553        | a3            | 531        |
|        | a4               | 541        | a4            | 513        |
|        | a5               | 517        | a5            | 411        |
|        | a6               | 534        | a6            | 539        |
|        | a7               | 563        | a7            | 531        |
|        |                  | 547        | a8            | 518        |
| Mean   |                  | 543.37     |               | 447        |
| Std dev|                  | 13.85      |               | 41.28      |

Approximately 18% of cells are lost.

In one embodiment, shrimp alkaline phosphatase activity loss is measured in microchannels of design one. It is similar to the embodiment for the horseradish peroxidase assay, only SAP is known to be very heat labile. A 200 mW laser, 980 nm wavelength, laser was used in design 1 in PDMS, with varying flow rates. Exposure of SAP molecules to laser beam was controlled by varying flow rates:

5 µL/minute v=6.4e−4 m/s time=0.15625 seconds
2 µL/minute v=2e−4 m/s time=0.5 seconds
1 µL/minute v=1 e−4 m/s time=1 second The test procedure was conducted as follows:
  Set up a two fold dilution series with 100 µl of assay buffer in tube 1 and 50 µl in next 6 tubes
  Add 3 µl enzyme to tube1 and serially dilute 50 µl into 50 µl into 50 µl etc . . .
  Add 10 µl of tube 5 to 1 ml of assay buffer.
  Set the spectrophotometer to 405 nm
  Put the solution of step 3 into a cuvette and add 10 µl of 10× substrate.
  Keep the spectrophotometer on kinetics and press start.
Note: For Laser exposure the 10 µl of enzyme solution from step 3 is flown through the microchannels and the channels are flushed with 10 µl of assay buffer. The microchannels are designed in a manner to accommodate the waveguide from the laser as described above.

Figure 8:
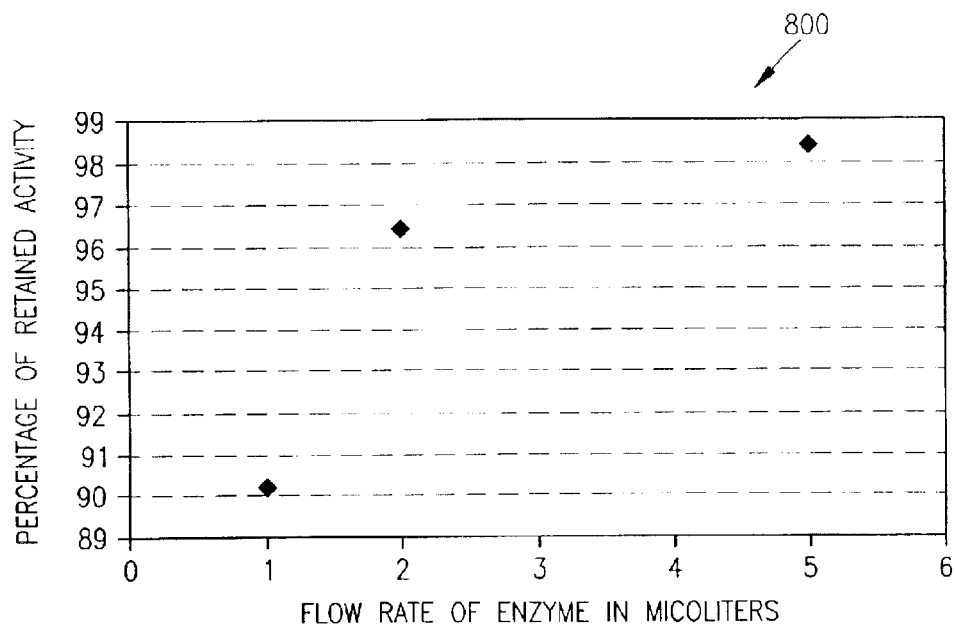
FIG. 8 is a graph of retained enzyme activity of a lysed cell versus flow rate for a given example.

Results are shown in FIG. 8 at 800. Remaining activity is shown, not loss in activity. Depending on the exposure length to the laser light, activity of the shrimp alkaline phosphatase was lost. However, the highest loss was as little as 10% (at a flow rate of 1 µL/min), where as at the highest flow rate (5 µL/min) only 3.5% were lost, which is within the error margin of the detection method. Thus, the laser lysis conditions have no or little denaturing effect on even labile proteins.

E. coli cell lysis in microchannels made of PDMS in the form of design one was also measured.

The conditions comprise a 200 mW laser, 980 nm wavelength, design 1 in PDMS with varying flow rates.

Figure 9:
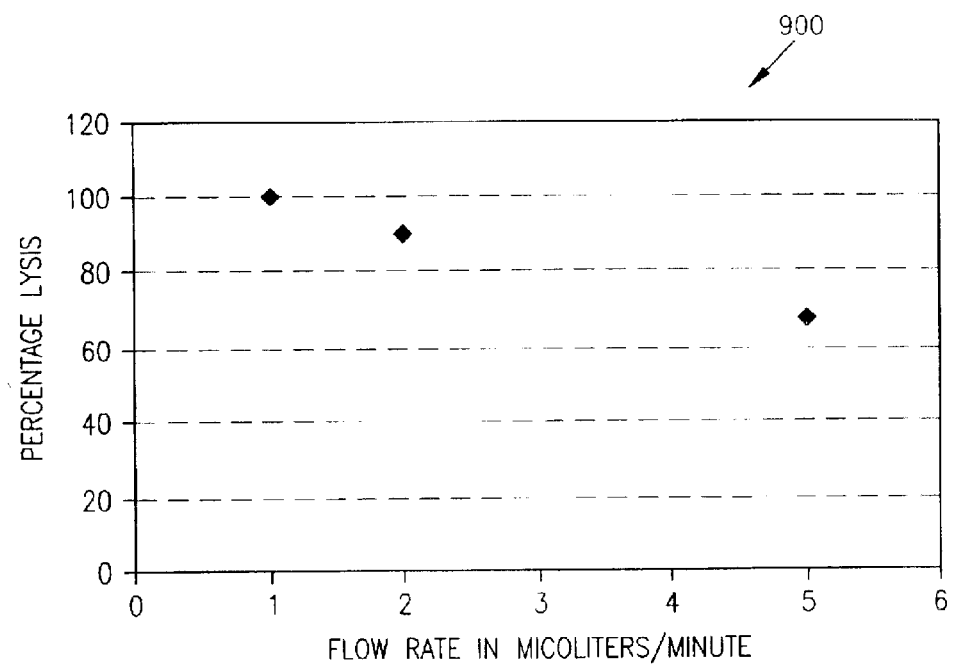
FIG. 9 is a graph of percentage of cell lysis versus flow rate for a given example.

5 µL/minute v=6.4e−4 m/s time=0.15625 seconds
2 µL/minute v=2e−4 m/s time=0.5 seconds
1 µL/minute v=1e−4 m/s time=1 second Results are shown in FIG. 9 at 900 as a percentage of cell lysis versus flow rate.

| Flow rate | % cell lysis |
|-----------|--------------|
| 5 µL/min  | 67           |
| 2 µL/min  | 90           |
| 1 µL/min  | 99.9         |

Depending on the flow rate studied, 67–99.9% cell lysis was obtained. Under the same conditions, loss in activity of a fragile enzyme (shrimp alkaline phosphatase) was found to be equal or less than 10%. These results were obtained with a sub-optimal laser wavelength that was used for the current experiment, i.e. 980 nm wavelength, even though it was determined previously that a wavelength between 1250 and 1550 would be better. Since those lasers were not available yet as miniaturized version, experiments were carried out at the lower wavelength, but therefore at higher power setting, i.e. 200 mW.

The microchannel system is much more efficient than the macroscopic set up represented in FIG. 1. Efficient cell lysis will be obtainable using higher wavelength miniaturized lasers with fast flow rates (i.e. at least 5 μL/min) and minimal enzyme damage will occur under those conditions.

While certain parameters were used in experiments described herein, it is recognized that many other values for the parameters can be utilized to find an optimal set of parameters for each different type of cell. The cells utilized in the experiments consisted of cells with cell membranes, gram positive and gram negative bacteria as well as mammalian cells. It is anticipated that all different types of cells and virus particles may be utilized and parameters defined therefore. The same method and apparatus to determine the parameters is clearly applicable. In further embodiments, changes channel dimensions and use of other materials will be made.

Some results based on experiments have been described herein. These results are not to be taken as guarantees of performance, nor are the results to be taken as admissions that the invention will not work better. Some results were not as good as others, and such results may have been outliers in the data. It is in no way a representation that the invention will not work for certain types of cells.

What is claimed is:

1. A method of determining optimized laser parameters for effectively lysing cells with minimum power, the method comprising:

exposing a sample of cells to a laser light to lyse the cells;

varying at least one parameter of the laser, such parameters comprising power, wavelength and duration;

measuring damage to intracellular molecules of the cells at such varied parameters; and determining at least one optimized laser parameter based on the measured damage.

2. The method of claim 1, wherein the sample contains between approximately 80 to 2000 cells.

3. The method of claim 1, wherein the intracellular molecules comprise RNA.

4. The method of claim 3, wherein RNA released from the lysed cells is detected using a biosensor.

5. The method of claim 1, wherein measuring damage comprises measuring protein damage.

6. The method of claim 1, wherein the wavelength parameter is varied between approximately 500 nm and 3500 nm.

7. The method of claim 1, wherein the power parameter is varied between approximately 0.0 mW and 300 mW.

8. The method of claim 1, wherein the sample comprises approximately 25–150 cells per μL.

9. The method of claim 1, further comprising placing said sample of cells onto a hydrophobic surface prior to said exposing.

10. The method of claim 1, wherein said optimized parameters are effective in miniaturized devices.

11. The method of claim 1, further comprising measuring a denaturing effect of laser-induced cell lysis using a protein solution to further determine the parameters.

12. The method of claim 1, wherein the duration parameter is varied dependent on size of the sample.

13. The method of claim 1, wherein the cells comprise pathogenic microorganisms.

14. The method of claim 1, wherein the cells comprise *Bacillus cereus*, and wherein the optimized wavelength parameter comprises between approximately 1064 nm and 1250 nm.

15. The method of claim 1, wherein the cells comprise *Saccharomyces cerevisiae*, and wherein the optimized wavelength parameter comprises between approximately 1064 nm and 1250 nm.

16. The method of claim 1, wherein the cells comprise *Micrococcus luteus*, and wherein the optimized wavelength parameter comprises between approximately 1064 nm and 1250 nm.

17. A system for lysing cells, the system comprising:

a hydrophobic surface for supporting a sample of cells;

a laser having a power level and frequency optimized for effectively lysing a desired cell with minimum power; and means for directing the laser onto cells supported on said hydrophobic surface.

18. The system of claim 17, wherein the means for directing the laser onto cells supported on said hydrophobic surface comprises a mirror and a lens.

19. The system of claim 17, further comprising means for collecting protein from lysed cells.

20. The system of claim 19, wherein the laser has a power level variable between approximately 0.0 mW and 300 mW.

21. The system of claim 17, wherein the hydrophobic surface comprises a surface wrapped in a layer of parafilm.

22. The system of claim 21, wherein the sample of cells comprises cells in an aqueous solution.

23. The system of claim 22, wherein the sample of cells forms a sphere with least contact area to the parafilm surface.

24. The system of claim 17, wherein the desired cell to be lysed comprises a cell wall that is breached by the laser.

25. The system of claim 17, wherein the laser lyses cells without cell walls.

26. A method for lysing cells, the method comprising:

diluting a sample of cells;

placing the diluted sample on a hydrophobic surface; and exposing the cells to a laser having a power level and frequency optimized to effectively lyse the cells with minimum power.

27. The method of claim 26, wherein the laser provides light having a wavelength between approximately 900 nm and 3500 nm.

28. The method of claim 26, wherein the duration of said exposing is varied dependent on dimensions of the surface.

29. The method of claim 26, wherein the sample of cells is diluted with Tryptic Soy broth.

30. The method of claim 26, wherein the diluted sample of cells comprises concentrations of approximately 25–150 cells/μL.

31. A method of determining parameters for lysing cells, the method comprising:

a) diluting cells in a water based solution;

b) placing a sample of the cells on a hydrophobic surface;

c) exposing the sample of cells to a laser at a first set of parameters comprising power, wavelength and duration to lyse the cells;

d) measuring effectiveness of the lysing; and e) repeating b, c, and d with different laser parameters to determine an optimized set of parameters to effectively lyse said cells with minimum power.

32. The method of claim 31, wherein the optimized set of parameters is determined by effectiveness of the lysing.

33. The method of claim 31, wherein effectiveness of the lysing is measured by the ability of the sample of cells to grow colonies after laser exposure.

34. The method of claim 31, wherein effectiveness of the lysing is measured by use of biosensor assay.

35. The method of claim 31, further comprising using positive controls.

36. The method of claim 35, wherein the positive controls comprise disruption of cells via sonication to completely lyse cells.

37. A system for lysing cells, the system comprising:
a substrate;
an inlet formed in the substrate;
an outlet formed in the substrate;
a channel formed in the substrate between the inlet and the outlet for transporting cells between the inlet and the outlet; and
a laser integrated into the substrate proximate a portion of the channel, the laser having a wavelength and power optimized for effectively lysing cells with minimum power within the channel.

38. The system of claim 37 wherein the substrate is formed of silicon.

39. The system of claim 37 wherein the channel is formed of polydimethylsiloxane.

* * * * *

UNITED STATES PATENT AND TRADEMARK OFFICE
CERTIFICATE OF CORRECTION

PATENT NO. : 6,815,209 B2
DATED : November 9, 2004
INVENTOR(S) : Baeumner et al.

It is certified that error appears in the above-identified patent and that said Letters Patent is hereby corrected as shown below:

Title page,
Item [75], Inventors, delete "Baeummer" and insert -- Baeumner -- in its place.

Signed and Sealed this

Tenth Day of May, 2005

JON W. DUDAS
*Director of the United States Patent and Trademark Office*